(12) United States Patent
Estevez

(10) Patent No.: US 6,822,343 B2
(45) Date of Patent: Nov. 23, 2004

(54) GENERATING ELECTRIC POWER IN RESPONSE TO ACTIVITY OF A BIOLOGICAL SYSTEM

(75) Inventor: Leonardo W. Estevez, Rowlett, TX (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 10/349,129

(22) Filed: Jan. 22, 2003

(65) Prior Publication Data

US 2003/0168861 A1 Sep. 11, 2003

Related U.S. Application Data

(60) Provisional application No. 60/360,969, filed on Feb. 28, 2002.

(51) Int. Cl.[7] .............................. F02C 6/18; A61N 1/00; A61N 1/36; F04B 9/14; F04B 17/00
(52) U.S. Cl. ............................. 290/1 R; 607/35; 607/2; 322/3; 417/374; 417/394
(58) Field of Search ......................... 607/1, 2, 9, 35; 322/1, 3; 290/1 R; 417/374, 394

(56) References Cited

U.S. PATENT DOCUMENTS

| | | | |
|---|---|---|---|
| 3,048,121 A | 8/1962 | Sheesley | 417/394 |
| 3,421,512 A | 1/1969 | Frasier | 607/35 |
| 3,456,134 A | 7/1969 | Kowen | 607/35 |
| 3,554,199 A | 1/1971 | Auphan | 607/19 |
| 3,563,245 A | 2/1971 | McLean et al. | 607/35 |
| 3,659,615 A | 5/1972 | Enger | 607/35 |
| 4,250,872 A | 2/1981 | Tamari | 600/16 |
| 4,453,537 A | 6/1984 | Spitzer | 623/3.12 |
| 4,662,829 A | 5/1987 | Nehring | 417/395 |
| 4,740,711 A | 4/1988 | Sato et al. | 290/52 |
| 5,109,843 A | 5/1992 | Melvin et al. | 607/2 |
| 5,129,789 A | 7/1992 | Thornton et al. | 417/53 |
| 5,431,694 A * | 7/1995 | Snaper et al. | 607/35 |
| 5,443,440 A * | 8/1995 | Tumey et al. | 601/152 |
| 5,769,801 A * | 6/1998 | Tumey et al. | 601/152 |
| 5,810,015 A * | 9/1998 | Flaherty | 128/697 |
| 5,923,619 A * | 7/1999 | Knapen et al. | 368/64 |
| 5,931,797 A * | 8/1999 | Tumey et al. | 601/152 |
| 3,486,506 A | 12/1999 | Auphan | 607/19 |
| 6,087,750 A * | 7/2000 | Raad | 310/152 |
| 6,110,143 A * | 8/2000 | Kamen | 604/97 |
| 6,293,771 B1 * | 9/2001 | Haney et al. | 417/374 |
| 6,464,476 B2 * | 10/2002 | Ross et al. | 417/478 |
| 6,555,926 B2 * | 4/2003 | Gondron | 290/1 R |
| 6,620,121 B1 * | 9/2003 | McCotter | 604/6.11 |
| 6,672,847 B2 * | 1/2004 | Dooley | 417/412 |
| 6,689,074 B2 * | 2/2004 | Seto et al. | 601/5 |

OTHER PUBLICATIONS

Unknown, *Microgenerators*, Kinetron, http://kinetron.,n1/b_produc/b1.htm, 1 p, printed Dec. 17, 2001.
Kinetron..n1/b_produce/b1htm, 1 p. printed Dec. 17, 2001.
Unknow, Press Release, Maxwell Technologies, ONEMOCALL Form Alliance to Combine Energy Generation and Storage Technologies for Electronic Devices, Maxwell Technologies, 2 pp. dated May 2000, printed Jan. 8, 2002.

* cited by examiner

Primary Examiner—Nicholas Ponomarenko
Assistant Examiner—Pedro J. Cuevas
(74) Attorney, Agent, or Firm—Robert D. Marshall, Jr.; W. James Brady, III; Frederick J. Telecky, Jr.

(57) ABSTRACT

A device for generating electricity includes a first portion including a first wall defining a first fluid passage and a second portion including a second wall defining a second fluid passage. A generator is coupled between the first and second portions and is capable of generating electricity in response to flow of a fluid from the first fluid passage to the second fluid passage through the generator. The generator is capable of generating electricity sufficient to power one or more electronic devices coupled to the generator. The flow of the fluid is associated with activity of a biological system of a user, for example, cardio-pulmonary activity of the user.

38 Claims, 1 Drawing Sheet

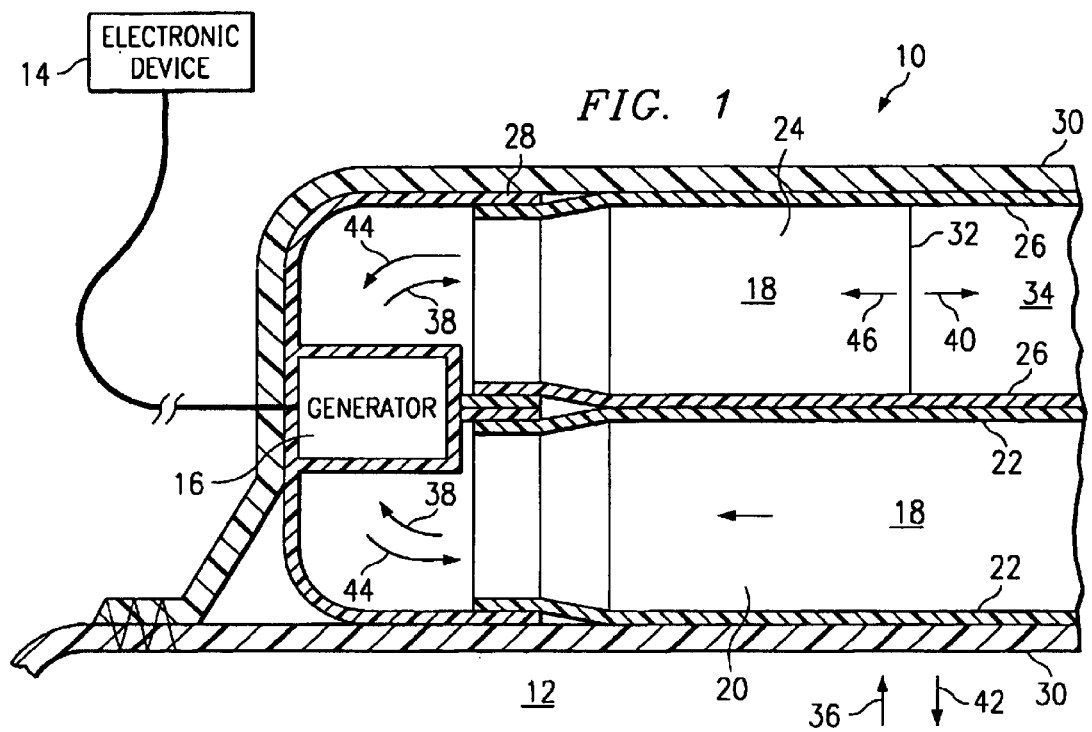
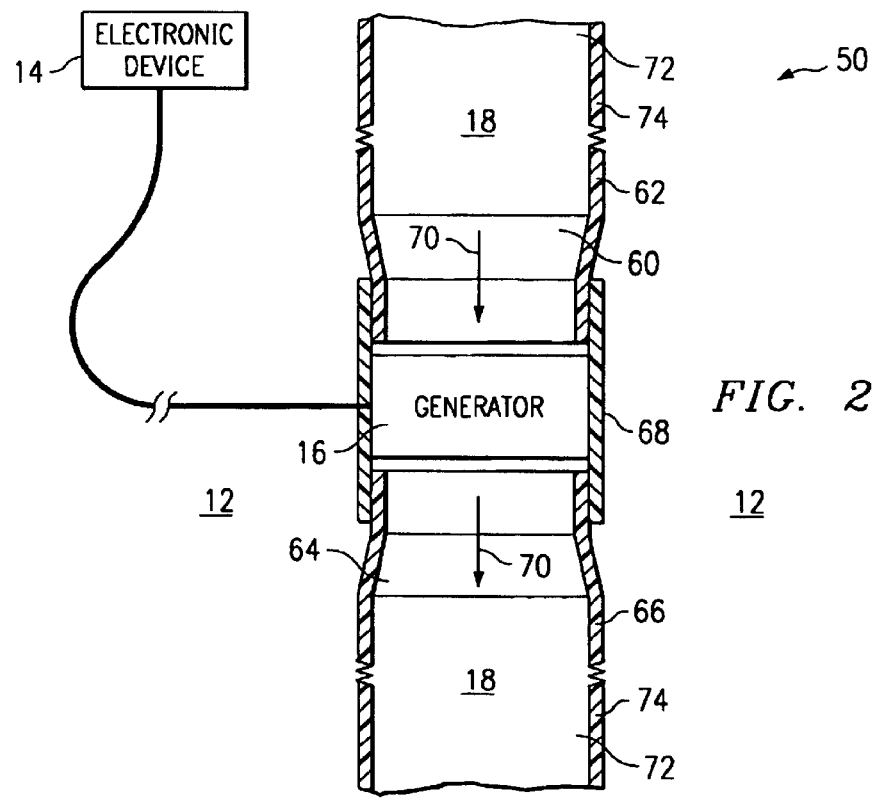

GENERATING ELECTRIC POWER IN RESPONSE TO ACTIVITY OF A BIOLOGICAL SYSTEM

This application claims priority under 35 USC §119(e) (1) of Provisional Application No. 60/360,969, filed Feb. 28, 2002.

TECHNICAL FIELD OF THE INVENTION

This invention relates in general to power generation and more particularly to generating electric power in response to activity of a biological system.

BACKGROUND OF THE INVENTION

Small-scale electric generators have been developed to generate electric power at levels suitable for powering small-scale electronic devices. For example, a small-scale generator developed by KINETRON B. V. provides an auto-generating power supply system for small-scale electronic devices, such as quartz wristwatches, that transforms kinetic energy into electric energy. When a wristwatch incorporating the system is worn, the combination of wrist movements and gravity causes an eccentric mass to rotate and thereby accelerate a multipolar magnet to generate electricity. The generated electricity is stored in an accumulator for subsequent use in powering time-keeping or other operations of the wristwatch.

SUMMARY OF THE INVENTION

According to the present invention, disadvantages and problems associated with previous techniques for generating electric power may be substantially reduced or eliminated.

According to one embodiment of the present invention, a device for generating electricity in response to cyclical activity of a biological system of a user includes an inner portion having a first proximity to a surface of the user's body and including a first collapsible wall defining a inner fluid passage extending in a first direction substantially parallel to the surface of the user's body. The inner portion is capable of expelling at least some of a fluid contained in the inner fluid passage from the inner fluid-passage in response to an external force applied to the first wall in a direction substantially perpendicular to the first direction of the inner fluid passage, the applied external force resulting from expansion of the surface of the user's body in connection with the activity of a biological system of the user. The inner portion is also capable of receiving the expelled fluid back into the inner fluid passage in response to the applied external force decreasing as a result of contraction of the surface of the user's body in connection with the activity of the biological system. An outer portion of the device has a second proximity to the surface of the user's body and includes a second collapsible wall defining an outer fluid passage extending in a second direction substantially parallel to the surface of the user's body, the second proximity being a greater distance from the surface of the user's body than the first proximity. The outer portion is capable of receiving the fluid expelled from the inner fluid passage of the inner portion in response to the applied external force. The outer portion is also capable of returning the expelled fluid to the inner fluid passage in response to the applied external force decreasing. A generator coupled between the inner portion and the outer portion is capable of generating electricity according to repeated flow of the fluid from the inner fluid passage of the inner portion to the outer fluid passage of the outer portion through the generator in response to cyclical activity of the biological system. The generator in combination with the inner and outer portions is capable of generating electricity sufficient to power one or more electronic devices coupled to the generator.

According to another embodiment of the present invention, a device for generating electricity according to flow of a fluid within a fluid passage of a user's body includes an upstream portion including a first wall defining a first fluid passage extending between first and second ends of the upstream portion of the device in a direction substantially parallel to the user's fluid passage. The first end of the upstream portion of the device is capable of receiving a fluid flowing in an upstream portion of the user's fluid passage according to the flow of the fluid. The second end of the upstream portion of the device is capable of emitting the received fluid according to the flow of the fluid. A downstream portion of the device includes a second wall defining a second fluid passage extending between first and second ends of the downstream portion of the device in the direction substantially parallel to the user's fluid passage. The first end of the downstream portion of the device is capable of receiving the fluid emitted from the upstream portion of the device according to the flow of the fluid. The second end of the downstream portion of the device is capable of emitting the received fluid to a downstream portion of the user's fluid passage according to the flow of the fluid. A generator coupled between the upstream and downstream portions of the device is capable of generating electricity in response to the flow of the fluid from the first fluid passage of the upstream portion of the device to the second fluid passage of the downstream portion of the device through the generator. The generator in combination with the upstream and downstream portions of the device is capable of generating electricity sufficient to power one or more electronic devices coupled to the generator.

Particular embodiments of the present invention may provide one or more technical advantages that are readily apparent to those skilled in the art from the figures, descriptions, and claims included herein. Certain embodiments may provide some, all or none of these technical advantages.

BRIEF DESCRIPTION OF THE DRAWINGS

To provide a more complete understanding of the present invention and the features and advantages thereof, reference is made to the following description taken in conjunction with the accompanying drawings, in which:

FIG. 1 illustrates a first example device for generating electric power in response to activity of a biological system; and FIG. 2 illustrates a second example device for generating electric power in response to activity of a biological system.

DETAILED DESCRIPTION OF EXAMPLE EMBODIMENTS

FIG. 1 illustrates a first example device 10 for generating electric power in response to activity of a biological system. In one embodiment, device 10 is used to generate electric power in response to the breathing of a user 12, for example, for use in powering one or more electronic devices 14. Device 10 includes an electric generator 16 that, in general, uses mechanical energy associated with the movement of a fluid 18 through generator 16 to generate electricity for powering one or more electronic devices 14. For example, generator 16 may include a direct current (DC) generator with a turbine that, in response to movement of fluid 18 through generator 16 as user 12 breathes, rotates a wire coil around an axis and through a magnetic field created by permanent magnets to induce an electric current in the wire coil. The electric current generated in the wire coil may be used, substantially immediately or after storage for some period of time, to power one or more electronic devices 14. Although a DC generator is described merely as one example, the present invention contemplates device 10 including any suitable generator 16 according to particular needs. For example, micro electrical mechanical systems (MEMS) technology may provide one or more generators 16 for use in embodiments of the present invention. Suitable generators 16 are well known to those skilled in the art, and those skilled in the art will appreciate that the present invention encompasses all such generators 16 that are currently available or may be developed in the future as technology further advances, whether or not explicitly described herein.

In one embodiment, device 10 includes an inner collapsible fluid-containing portion 20 having a cylindrical or other suitable wall 22, an outer collapsible fluid-containing portion 24 having a cylindrical or other suitable wall 26, and a coupler 28 that houses generator 16 and couples inner fluid-containing portion 20 to outer fluid-containing portion 24. Fluid-containing portions 20 and 24 may be integrated with coupler 28 or may be coupled in any suitable manner to coupler 28, for example, ultrasonically welded, glued, force-fitted, or otherwise coupled. If appropriate, fluid-containing portions 20 and 24 may be coupled to one another along walls 22 and 26, respectively, for example, to help stabilize the overall configuration of inner fluid-containing portion 20, outer fluid-containing portion 24, and coupler 28. Device 10 may include a flexible sleeve 30 that can be worn comfortably about the chest cavity of user 12 while supporting the configuration of inner fluid-containing portion 20, outer fluid-containing portion 24, and coupler 28. For example, sleeve 30 might be constructed of neoprene or any other fabric having appropriate elasticity, durability, breathability, or other desirable properties. Sleeve 30 may be integral to a belt, shirt, vest, or other wearable item, according to particular needs.

Preferably, inner fluid-containing portion 20 may be substantially filled with a substantially non-compressible fluid 18 such as water or another suitable liquid, while fluid-containing portion 20 may be filled with both fluid 18 (in a first region defined by fluid interface 32) and a substantially compressible fluid 34 such as air or another suitable gas (in a second region defined by fluid interface 32 adjacent the first region). As user 12 breathes in the chest cavity of user 12 expands (as indicated by arrow 36), causing at least some fluid 18 in inner fluid-containing portion 20 to move through generator 16 to outer fluid-containing portion 24 (as indicated by arrows 38) and fluid interface 32 to move in a first direction (as indicated by arrow 40). Wall 26 of outer fluid-containing portion 24 may expand as a result. Conversely, as user 12 breathes out the chest cavity of user 12 contracts (as indicated by arrow 42), causing at least some fluid 18 in outer fluid-containing portion 24 to move through generator 16 to inner fluid-containing portion 20 (as indicated by arrows 44) and fluid interface 32 to shift in a second direction opposite the first direction (as indicated by arrow 46). Wall 26 of outer fluid-containing portion 24 may contract to help force fluid 18 back into inner fluid-containing portion 20. Movement of fluid 18 through generator 16 from inner fluid-containing portion 20 to outer fluid-containing portion 24 as user 12 breathes in, from outer fluid-containing portion 24 to inner fluid-containing portion 20 as user 12 breathes out, or both may result in the generation of electric power. The total electric power generated may be seen to increase substantially linearly with the number of cycles (i.e. breaths).

The electricity generated as a result of the breathing of user 12 may be used substantially immediately as it is generated to power electronic device 14 or may be stored for a period of time in a battery, capacitor, or another appropriate rechargeable accumulator coupled between generator 16 and electronic device 14. An electronic device 14 may be any suitable electronic device, constrained only in that electronic device 14 should be able to operate using electric power available from generator 16. In embodiments in which the electric power that is generated may be stored for later use, electric power available from generator 16 may include stored electric power in addition to electric power currently being generated, such that a larger electronic device 14 may be used, electronic device 14 may be operated for a longer period of time, or more electronic devices 14 may be operated.

As particular non-limiting examples, device 10 may include a belt, shirt, vest, or other garment worn in a dark or poorly lit environment (e.g., at night, in a mine, in a cave, in deep water, etc.) and electronic device 14 may include a light for visibility and to indicate the location of user 12 while user 12 performs activities within that environment. Such activities may be vocational, recreational, emergency, or other suitable activities. For example, device 10 may include a wetsuit for deep sea diving associated with deep sea oil exploration, a first electronic device 14 within device 10 may include a light to provide user 12 increased visibility and to indicate the location of user 12 (e.g., for safety, rescue, or other purposes), a second electronic device 14 within device 10 may include a radio transmitter to further indicate the location of user 12 or a two-way radio transceiver to allow user 12 to interactively communicate with others; and a third electronic device 14 within device 10 may include a dive computer or other processing device for measuring and indicating depth, regulating the volume of air within a dive bladder or other buoyancy-compensation apparatus, or for any other diving-related purposes. Similarly, device 10 may include a wetsuit for scuba-diving and may include one or more of these electronic devices 14. As another example, device 10 may include a belt, shirt, vest, or other garment that user 12 can wear while exercising, and electronic device 14 may include a computer or other processing device suitable for keeping time, monitoring heartrate, calculating calories expended, or for any other exercise-related purposes. As yet another example, device 10 may include a life vest or other flotation device and may include one or more of a light, a radio transmitter or two-way radio, and a global positioning system (GPS) receiver. Similarly, device 10 may include a belt, shirt, vest, or other garment that can be worn if user 12 becomes lost in a remote wilderness area and may include one or more of these electronic devices 14. As indicated above, these particular examples are not intended to limit the scope of the present invention and are provided for purposes of illustration. Those skilled in the art will readily appreciate that the present invention is meant to encompass all appropriate devices 10 and appropriate associated electronic devices 14.

Although only a single generator 16 is illustrated and described, any suitable number of generators 16 may be incorporated in device 10 according to particular needs and physical constraints, for additional power generation. For example, device 10 might include a second coupler 28 and associated generator 16 at an opposite end (not shown) of device 10, such that fluid 34 is confined between two opposing fluid interfaces 32 within outer fluid-containing portion 24. As another example, a series of parallel configurations of inner fluid-containing portion 22, outer fluid-containing portion 24, and coupler 28 might be included in device 10. The present invention contemplates any number and arrangement of generators 16 suitable to power one or more electronic devices 14 associated with user 12, where each generator 16 may power one or more electronic devices 14 and each electronic device 14 may rely on power from one or more generators 16.

Furthermore, although device 10 is described as generating electric power in response to cyclical movements associated with the breathing of user 12, device 10 may be analogously used to generate electric power in response to any appropriate cyclical movements of user 12. For example, device 10 may includes a cuff or other structure (e.g., integral to sleeve 30) that can be secured about the upper arm or leg of user 12 to generate electric power in response to repeated flexion and extension of muscles of the upper arm or leg, respectively. Such cyclical movements may occur naturally during exercise or other activities or may be undertaken for the express purpose of generating electric power, for example, in an emergency situation. The present invention is intended to encompass any suitable configuration of inner fluid-containing portion 20, outer fluid-containing portion 24, and coupler 28, including its associated generator 16, within a device 10 that can be coupled to the body of a user 12 to generate electric power based on cyclical movement of user 12.

FIG. 2 illustrates a second example device 50 for generating electric power in response to an activity of a biological system. In one embodiment, device 50 is used to generate electric power in response to flow of blood within an artery or other blood vessel, flow of air within a nasal passage, or other flow of fluid 18 within a portion of the body of user 12. Similar to device 10 described above, device 50 includes a suitable electric generator 16 that, in general, uses mechanical energy associated with the movement of fluid 18 through generator 16 to generate electricity for powering one or more electronic devices 14. Also similar to device 50, device 10 includes a first fluid-containing portion 60 having a cylindrical or other suitable wall 62, a second fluid-containing portion 64 having a cylindrical or other suitable wall 66, and a coupler 68 that houses generator 16 and couples first fluid-containing portion 60 to second fluid-containing portion 64. Fluid-containing portions 60 and 64 may be integrated with coupler 68 or may be coupled in any suitable manner to coupler 68, for example, ultrasonically welded, glued, force-fitted, or otherwise coupled. As fluid 18 flows from first fluid-containing portion 60 to second fluid-containing portion 64 through generator 16 (as indicated by arrows 70), electricity is generated.

In one embodiment, for example, as shown in FIG. 2, an artery or other blood vessel 72 may be severed and device 50 inserted into blood vessel 72 as a shunt, with walls 62 and 66 of fluid-containing portions 60 and 64 being stitched or otherwise attached to the severed and thus discontinuous walls 74 of blood vessel 72. As another example, device 50 may be inserted and secured within blood vessel 72, using stitches or otherwise, such that walls 74 remain substantially continuous. In either case, the uni-directional periodic movement of blood through generator 16 in response to the cardio-pulmonary activity of user 12 is converted to electricity for powering one or more electronic devices 14. As yet another example, device 50 may be inserted and secured, such as through simple force-fitting, within a nasal passage (not shown) of user 12. In this case, the movement of air through generator 16 in response to the cardio-pulmonary activity of user 12 is converted to electricity for powering one or more electronic devices 14. Although arrows 70 flow of fluid 18 is indicated as being uni-directional as in the case of blood flow within blood vessel 72, flow of air in a nasal passage may be consistently uni-directional (e.g., where user 12 consistently inhales through the nose but exhales through the mouth or consistently inhales through the mouth but exhales through the nose), consistently bi-directional (e.g., where user 12 consistently both inhales and exhales through the nose), or both uni-directional and bi-directional at various times. Device 50 may be used in any environment having any appropriate flow characteristics. Similar to device 10, the total electric power generated using device 50 may be seen to increase substantially linearly with the volume of fluid 18 passing through generator 16 over time.

Electricity generated as a result of fluid flow through generator 16 may be used substantially immediately, as it is generated, to power electronic device 14 or may be stored for some period of time in a battery, capacitor, or another appropriate rechargeable accumulator coupled between generator 16 and electronic device 14. Electronic device 14 may be any suitable electronic device, constrained only in that electronic device 14 should be able to operate using electric power available from generator 16. In embodiments in which the electric power that is generated may be stored for later use, electric power available from generator 16 may include stored electric power in addition to the electric power currently being generated, such that a larger electronic device 14 may be used, electronic device 14 may be operated for a longer period of time, or more electronic devices 14 may be operated. Any number and arrangement of generators 16 suitable to power one or more electronic devices 14 associated with user 12 may be used. Each generator 16 may power one or more electronic devices 14 and each electronic device 14 may rely on power from one or more generators 16. Furthermore, multiple devices 50 may be used in combination to power one or more electronic devices 14. For example, devices 50 could be inserted into multiple blood vessels or into both nasal passages of user 12.

As particular non-limiting examples, electronic device 14 may include any of those described above with reference to FIG. 1. For example, electronic device 14 may include a light, radio transmitter, two-way radio transceiver, GPS receiver, computer or other processing device, or any other appropriate electronic device. As a more particular example, device 50 may be implanted in or otherwise secured to an animal and electronic device 14 may include a radio transmitter to generate a homing signal used to track the location of the animal for scientific, animal control, or other suitable purposes. Where device 50 is implanted in or otherwise secured to a human being, such a homing signal could be used for monitoring the location of a prisoner within a correctional facility or under house-arrest, in a work-release program, on parole or probation, or otherwise subject to limited freedoms. The ability to track such a prisoner relatively unobtrusively might allow more prisoners to take part in such programs, thereby minimizing burdens on the correctional system. Similarly, a homing signal could be used for monitoring the location of a suspect charged with a crime and out on bail, which might allow more suspects to be granted bail and also minimize burdens on the correctional system.

As another example, where device 50 is inserted in a blood vessel of user 12, an electronic device 14 might include a system also implanted in the body of user 12 to automatically monitor levels of certain substances (e.g., gases, sugars, enzymes, hormones, medicines, or other substances) in the blood and, if appropriate based on the determined level, release additional substances into the blood stream. Released substances may be the same as or different than monitored substances. For example, where the level of a monitored hormone is found to be low, additional quantities of the monitored hormone may be released or quantities of a second hormone known to increase levels of the monitored hormone may be released. Instead or in addition to releasing a substance into the blood, the system may include a transmitter suitable to notify user 12 of a condition, such that user 12 can take remedial action, or to notify an external auto-injection system such that the external auto-injection system should supply the appropriate substance. Instead of or in addition to releasing a substance into the blood, the system may operate to filter a monitored substance from the blood in response to determining that the level of the monitored substance is too high or may operate to filter a substance from too high on a substantially continuous basis regardless of any such monitoring. For example, filtering may be desirable to limit blood cholesterol levels.

As another example, where device 50 is inserted in a blood vessel of user 12 in connection with implantation of a cardiac pacemaker, an electronic device 14 may include the pacemaker itself. In this case, electricity from generator 16 may be used to power the pacemaker on an ongoing bases. Instead or in addition, electricity from generator 16 could be stored in a suitable accumulator and used in case of cardiac arrest to more fully stimulate the heart of user 12 (e.g., where the pacemaker acts similar to a defibrillator device). Cardiac arrest might be determined based on an absence of electricity being received at the pacemaker from generator 16 or in any other suitable manner. Whether or not a pacemaker is powered using electricity from generator 16, an electronic device 14 used in connection with the pacemaker might include a computer or other processing device for monitoring the operation of the pacemaker and providing information about such operation to user 12.

As another example, where device 50 is inserted in the nasal passage of user 12, a first electronic device 14 also within the nasal passage may include a computer or other processing device to extract information about speech of user 12 (e.g., audio signals based on variations in the voltage generated as a result of variations in the flow of air through generator 16 and extracted as features), and a second electronic device also within the nasal passage may include a small wireless microphone or other radio transmitter capable of transmitting the extracted information to another larger radio transmitter within the coat pocket or otherwise hidden in the clothing of user 12. This might be useful in environments in which user 12 does not want others in the vicinity to know that user 12 is communicating. Furthermore, the same or a different electronic device 14 may be used to receive similar signals and convert the received signals into vibrations that user 12 can understand.

As yet another example, where device 50 is inserted in the nasal passage of user 12, electricity may be generated in bursts according to a regulated flow of air through generator 16 and the corresponding measured voltages used as a form of communication. For example, user 12 could exhale through the nose in regulated bursts corresponding to Morse code or other appropriate signals while inhaling only through the mouth. As described above, an electronic device 14 also within the nasal passage may include a wireless transmitter to transmit these voltages to a larger radio transmitter within the coat pocket or otherwise hidden in the clothing of user 12. In addition to environments in which secrecy is a goal, this might be useful to allow a user 12 that cannot speak properly or at all to communicate with others. Also as described above, the same or a different electronic device 14 may be used to receive similar signals and convert the received signals into vibrations understandable to user 12 can understand. In addition to environments in which secrecy is a goal, this might be useful to allow a user 12 that cannot hear properly or at all to communicate with others.

As indicated above, these particular examples are not intended to limit the scope of the present invention and are provided for purposes of illustration. Those skilled in the art will appreciate that the present invention is meant to encompass all suitable devices 50 and appropriate associated electronic devices 14.

Although the present invention has been described with several embodiments, a plethora of changes, substitutions, variations, alterations, and modifications may be suggested to one skilled in the art, and it is intended that the invention encompass all such changes, substitutions, variations, alterations, and modifications as fall within the spirit and scope of the appended claims.

What is claimed is:

1. A device for generating electricity in response to cyclical activity of a biological system of a user, comprising:

an inner portion having a first proximity to a surface of the user's body and comprising a first collapsible wall defining a inner fluid passage extending in a first direction substantially parallel to the surface of the user's body, the inner portion operable to:

expel at least some of a fluid contained in the inner fluid passage from the inner fluid-passage in response to an external force applied to the first wall in a direction substantially perpendicular to the first direction of the inner fluid passage, the applied external force resulting from expansion of the surface of the user's body in connection with the activity of a biological system of the user; and receive the expelled fluid back into the inner fluid passage in response to the applied external force decreasing as a result of contraction of the surface of the user's body in connection with the activity of the biological system;

an outer portion having a second proximity to the surface of the user's body and comprising a second collapsible wall defining an outer fluid passage extending in a second direction substantially parallel to the surface of the user's body, the second proximity being a greater distance from the surface of the user's body than the first proximity, the outer portion operable to:

receive the fluid expelled from the inner fluid passage of the inner portion in response to the applied external force; and return the expelled fluid to the inner fluid passage in response to the applied external force decreasing; and a generator coupled between the inner portion and the outer portion, the generator operable to generate electricity according to repeated flow of the fluid from the inner fluid passage of the inner portion to the outer fluid passage of the outer portion through the generator in response to cyclical activity of the biological system, the generator being operable in combination with the inner portion and outer portion to generate electricity sufficient to power one or more electronic devices coupled to the generator.

2. The device of claim 1, wherein:
the device comprises a flexible sleeve suitable to be worn about the user's chest, the sleeve supporting the first portion, the second portion, and the generator;
the activity comprises breathing;
the external force applied to the first wall of the inner portion results from expansion of the user's chest cavity as the user inhales; and
the applied external force decreases as a result of contraction of the user's chest cavity as the user exhales.

3. The device of claim 1, wherein:
the device comprises a flexible cuff suitable to be worn about a limb of the user, the cuff supporting the first portion, the second portion, and the generator;
the activity comprises cyclical flexion and extension of a muscle of the user's limb;
the external force applied to the first wall off the inner portion results from expansion of the surface of the user's limb as the user flexes the muscle of the user's limb; and
the applied external force decreases as a result of extension of the muscle of the user's limb.

4. The device of claim 1, wherein the generator comprises a direct current (DC) generator comprising a turbine operable, in response to the flow of the fluid from the inner fluid passage to the outer fluid passage through the generator, to rotate a wire coil around an axis and through a magnetic field created by permanent magnets to induce an electric current in the wire coil.

5. The device of claim 1, wherein the generator is further operable to generate electricity according to repeated return of the expelled fluid from the outer fluid passage of the outer portion to the inner fluid passage of the inner portion through the generator in response to cyclical activity of the biological system.

6. The device of claim 1, wherein the device comprises a plurality of sets of inner portions, outer portions, and generators, each set having substantially the same configuration and operating in substantially the same manner, the plurality of sets operable in cooperation to generate electricity sufficient to power one or more electronic devices.

7. The device of claim 1, further comprising a coupler operable to house the generator and to couple the inner portion to the outer portion.

8. The device of claim 1, wherein the fluid comprises water.

9. The device of claim 1, wherein:
the fluid comprises water and the outer portion is further operable to contain air within the outer fluid passage, the air being in contact with the water at a fluid interface within the outer fluid passage;
the flow of the expelled water from the inner fluid passage to the outer fluid passage causes the fluid interface to move away from the generator along the second direction of the outer fluid passage; and
return of the expelled water to the inner fluid passage from the outer fluid passage causes the fluid interface to move toward the generator along the second direction of the outer fluid passage.

10. The device of claim 1, further comprising the one or more electronic devices coupled to the generator, each electronic device capable of operating at least in part using the electricity generated by the generator.

11. The device of claim 10, wherein the one or more electronic devices comprise at least one of:
a light;
a radio transmitter;
a two-way radio transceiver;
a global positioning system (GPS) receiver; and
a computer processing device.

12. A device for generating electricity according to flow of a fluid within a fluid passage of a user's body, comprising:
an upstream portion comprising a first wall defining a first fluid passage extending between first and second ends of the upstream portion of the device in a direction substantially parallel to the user's fluid passage, the first end of the upstream portion of the device being operable to receive a fluid flowing in an upstream portion of the user's fluid passage according to the flow of the fluid, the second end of the upstream portion of the device being operable to emit the received fluid according to the flow of the fluid;
a downstream portion comprising a second wall defining a second fluid passage extending between first and second ends of the downstream portion of the device in the direction substantially parallel to the user's fluid passage, the first end of the downstream portion of the device being operable to receive the fluid emitted from the upstream portion of the device according to the flow of the fluid, the second end of the downstream portion of the device being operable to emit the received fluid to a downstream portion of the user's fluid passage according to the flow of the fluid; and
a generator coupled between the upstream and downstream portions of the device, the generator operable to generate electricity in response to the flow of the fluid from the first fluid passage of the upstream portion of the device to the second fluid passage of the downstream portion of the device through the generator, the generator being operable in combination with the upstream and downstream portions of the device to generate electricity sufficient to power one or more electronic devices coupled to the generator.

13. The device of claim 12, wherein the fluid comprises the user's blood, the user's fluid passage comprises a blood vessel, and the flow of the fluid is the flow of the user's blood within the user's blood vessel.

14. The device of claim 12, wherein the fluid comprises air, the user's fluid passage comprises a nasal passage, and the flow of the fluid is the flow of the user's blood within the user's nasal passage.

15. The device of claim 14, wherein:
the flow of the fluid is associated with exhalation of the air from the user's body through the user's nasal passage; and
the generator is further operable to generate electricity according to a flow of fluid associated with inhalation of air into the user's body through the user's nasal passage.

16. The device of claim 12, wherein the generator comprises a direct current (DC) generator comprising a turbine operable, in response to the flow of the fluid through the generator, to rotate a wire coil around an axis and through a magnetic field created by permanent magnets to induce an electric current in the wire coil.

17. The device of claim 12, further comprising a coupler operable to house the generator and to couple the upstream portion to the downstream portion.

18. The device of claim 12, wherein the device comprises a plurality of sets of upstream portions, downstream portions, and generators, each set having substantially the same configuration and operating in substantially the same manner, the plurality of sets operable in cooperation to generate electricity sufficient to power one or more electronic devices.

19. The device of claim 1, further comprising the one or more electronic devices coupled to the generator, each electronic device capable of operating at least in part using the electricity generated by the generator.

20. The device of claim 19, wherein the one or more electronic devices comprise at least one of:
- a radio transmitter;
- a two-way radio transceiver;
- a global positioning system (GPS) receiver;
- a cardiac pacemaker; and
- a computer processing device.

21. A method for generating electricity in response to cyclical activity of a biological system of a user, comprising:
  using an inner portion having a first proximity to a surface of the user's body and comprising a first collapsible wall defining a inner fluid passage extending in a first direction substantially parallel to the surface of the user's body:
    expelling at least some of a fluid contained in the inner fluid passage from the inner fluid-passage in response to an external force applied to the first wall in a direction substantially perpendicular to the first direction of the inner fluid passage, the applied external force resulting from expansion of the surface of the user's body in connection with the activity of a biological system of the user; and
    receiving the expelled fluid back into the inner fluid passage in response to the applied external force decreasing as a result of contraction of the surface of the user's body in connection with the activity of the biological system;
  using an outer portion having a second proximity to the surface of the user's body and comprising a second collapsible wall defining an outer fluid passage extending in a second direction substantially parallel to the surface of the user's body, the second proximity being a greater distance from the surface of the user's body than the first proximity:
    receiving the fluid expelled from the inner fluid passage of the inner portion in response to the applied external force; and
    returning the expelled fluid to the inner fluid passage in response to the applied external force decreasing; and
  using a generator coupled between the inner portion and the outer portion, generating electricity according to repeated flow of the fluid from the inner fluid passage of the inner portion to the outer fluid passage of the outer portion through the generator in response to cyclical activity of the biological system, the generated electricity being sufficient to power one or more electronic devices coupled to the generator.

22. The method of claim 21, wherein:
  the inner portion, outer portion, and generator are supported within a flexible sleeve worn about the user's chest;
  the activity comprises breathing;
  the external force applied to the first wall of the inner portion results from expansion of the user's chest cavity as the user inhales; and
  the applied external force decreases as a result of contraction of the user's chest cavity as the user exhales.

23. The method of claim 21, wherein:
  the inner portion, outer portion, and generator are supported within a flexible cuff worn about a limb of the user;
  the activity comprises cyclical flexion and extension of a muscle of the user's limb;
  the external force applied to the first wall of the inner portion results from expansion of the surface of the user's limb as the user flexes the muscle of the user's limb; and
  the applied external force decreases as a result of extension of the muscle of the user's limb.

24. The method of claim 21, wherein the generator comprises a direct current (DC) generator comprising a turbine operable, in response to the flow of the fluid from the inner fluid passage to the outer fluid passage through the generator, to rotate a wire coil around an axis and through a magnetic field created by permanent magnets to induce an electric current in the wire coil.

25. The method of claim 21, further comprising using the generator to generate electricity according to repeated return of the expelled fluid from the outer fluid passage of the outer portion to the inner fluid passage of the inner portion through the generator in response to cyclical activity of the biological system.

26. The method of claim 21, further comprising using a plurality of sets of inner portions, outer portions, and generators in cooperation to generate electricity sufficient to power one or more electronic devices, each set having substantially the same configuration and operating in substantially the same manner.

27. The method of claim 21, wherein the generator is housed within a coupler that couples the inner portion to the outer portion.

28. The method of claim 21, wherein the fluid comprises water.

29. The method of claim 21, wherein:
  the fluid comprises water and the outer portion is contains air within the outer fluid passage, the air being in contact with the water at a fluid interface within the outer fluid passage;
  the flow of the expelled water from the inner fluid passage to the outer fluid passage causes the fluid interface to move away from the generator along the second direction of the outer fluid passage; and
  return of the expelled water to the inner fluid passage from the outer fluid passage causes the fluid interface to move toward the generator along the second direction of the outer fluid passage.

30. The method of claim 21, wherein the one or more electronic devices comprise at least one of:
- a light;
- a radio transmitter;
- a two-way radio transceiver;
- a global positioning system (GPS) receiver; and
- a computer processing device.

31. A method for generating electricity according to flow of a fluid within a fluid passage of a user's body, comprising:
  using an upstream portion comprising a first wall defining a first fluid passage extending between first and second ends of the upstream portion of the device in a direction substantially parallel to the user's fluid passage:
    receiving, at the first end of the upstream portion of the device, a fluid flowing in an upstream portion of the user's fluid passage according to the flow of the fluid;
    emitting, from the second end of the upstream portion of the device, the received fluid according to the flow of the fluid; and
  using a downstream portion comprising a second wall defining a second fluid passage extending between first and second ends of the downstream portion of the device in the direction substantially parallel to the user's fluid passage:
  receiving, at the first end of the downstream portion of the device, the fluid emitted from the upstream portion of the device according to the flow of the fluid; and
  emitting to a downstream portion of the user's fluid passage, from the second end of the downstream portion of the device, the received fluid according to the flow of the fluid; and
using a generator coupled between the upstream and downstream portions of the device, generating electricity in response to the flow of the fluid from the first fluid passage of the upstream portion of the device to the second fluid passage of the downstream portion of the device through the generator, the generated electricity being sufficient to power one or more electronic devices coupled to the generator.

32. The method of claim 31, wherein the fluid comprises the user's blood, the user's fluid passage comprises a blood vessel, and the flow of the fluid is the flow of the user's blood within the user's blood vessel.

33. The method of claim 31, wherein the fluid comprises air, the user's fluid passage comprises a nasal passage, and the flow of the fluid is the flow of the user's blood within the user's nasal passage.

34. The method of claim 33, wherein:
  the flow of the fluid is associated with exhalation of the air from the user's body through the user's nasal passage; and
  the method further comprises also using the generator to generate electricity according to a flow of fluid associated with inhalation of air into the user's body through the user's nasal passage.

35. The method of claim 31, wherein the generator comprises a direct current (DC) generator comprising a turbine operable, in response to the flow of the fluid through the generator, to rotate a wire coil around an axis and through a magnetic field created by permanent magnets to induce an electric current in the wire coil.

36. The method of claim 31, wherein the generator is housed in a coupler that couples the upstream portion to the downstream portion.

37. The method of claim 31, further comprising using a plurality of sets of upstream portions, downstream portions, and generators to generate electricity sufficient to power one or more electronic devices, each set having substantially the same configuration and operating in substantially the same manner.

38. The method of claim 31, wherein the one or more electronic devices comprise at least one of:
  a radio transmitter;
  a two-way radio transceiver;
  a global positioning system (GPS) receiver;
  a cardiac pacemaker; and
  a computer processing device.

* * * * *